(12) United States Patent
Bacchetta et al.

(10) Patent No.: US 6,312,156 B1
(45) Date of Patent: Nov. 6, 2001

(54) INTRAORAL DENTAL RADIOGRAPHIC FILM PACKET WITH THERMOPLASTIC COMFORT ENHANCING RE-USABLE FRAME

(75) Inventors: Richard W. Bacchetta; Scott H. Schwallie, both of Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/534,370

(22) Filed: Mar. 24, 2000

(51) Int. Cl.[7] ........................................ A61B 6/14
(52) U.S. Cl. ................................. 378/169; 378/168
(58) Field of Search ............................ 378/169, 168

(56) References Cited

U.S. PATENT DOCUMENTS

| | | |
|---|---|---|
| 1,537,925 | 5/1925 | Bolin . |
| 1,631,497 | 6/1927 | Marler . |
| 2,084,092 | 6/1937 | Kenney . |
| 4,626,216 | 12/1986 | Strong-Grainger . |
| 4,791,657 | 12/1988 | Kirsch et al. . |
| 4,805,201 | 2/1989 | Strong-Grainger . |
| 4,847,884 | 7/1989 | Dove . |
| 4,852,143 | 7/1989 | Scheier et al. . |
| 4,911,871 | 3/1990 | Liese, Jr. . |
| 4,912,740 * | 3/1990 | Liese, Jr. ........................... 378/169 |
| 4,913,288 | 4/1990 | Tanaka . |
| 4,922,511 | 5/1990 | Gay . |
| 5,044,008 | 8/1991 | Jackson . |
| 5,077,779 | 12/1991 | Steinhausen, Jr. . |
| 5,285,491 | 2/1994 | Muylle et al. . |
| 5,784,433 | 7/1998 | Higa . |

* cited by examiner

Primary Examiner—Robert H. Kim
Assistant Examiner—Pamela R. Hobden
(74) Attorney, Agent, or Firm—Mark G. Bocchetti

(57) ABSTRACT

A reusable comfort enhancing frame for holding an intraoral x-ray film packet is taught which includes four integrally formed side members with a single contiguous perimetric contact surface having a generally rounded cross-sectional configuration and rounded comers. There is a pocket formed in the four integrally formed side members adapted to have the intraoral x-ray film packet inserted and retained therein, and removed therefrom. In one embodiment, there is a slot in one of the four integrally formed side members through which the intraoral x-ray film packet can be inserted to reside in the pocket. In a second embodiment, the pocket is a snap-in pocket comprising at least one lip element projecting from an interior peripheral wall of the four integrally formed side members and at least two snap-fit elements also projecting the interior peripheral wall of the four integrally formed side members.

10 Claims, 3 Drawing Sheets

INTRAORAL DENTAL RADIOGRAPHIC FILM PACKET WITH THERMOPLASTIC COMFORT ENHANCING RE-USABLE FRAME

FIELD OF THE INVENTION

The present invention relates generally to x-ray film packets and, in particularly, to frames with comfort enhancing features for intraoral radiographic film packets.

BACKGROUND OF THE INVENTION

A common problem experienced by people visiting the dentist is the discomfort and pain associated with the taking of dental x-rays caused by the positioning of intraoral radiographic film packets in the patient's mouth. The typical intraoral radiographic film packet includes relatively hard and/or relatively sharp edges that press against and irritate the gums and other oral soft tissue of the person whose teeth are being x-rayed. A variety of intraoral x-ray dental packets are known in the prior art which include features intended to be comfort enhancing. In addition, attempts have been made to create comfort-enhancing structures into which intraoral x-ray dental packets can be inserted prior to placement in the patient's mouth. One example of this type of structure is taught in U.S. Pat. No. 5,044,008 titled "Dental Film Cartridge Cushion," by Reginald B. Jackson, Aug. 27, 1991. Jackson utilizes a cartridge cushion comprising a foam sheet sandwich into which the x-ray dental packet is placed for the purpose of cushioning and increasing the comfort to the patient. Jackson requires the manual insertion of the x-ray packet into the cartridge cushion. Thus, Jackson adds significant bulk to the packet and enhances the possibility of triggering a gag reflex action in the patient. Additionally, after the cartridge cushion is removed from the packet, it would be possible to reuse the cartridge cushion. Reuse without sterilization would not be sanitary and there is no practical way of sterilizing Jackson's cartridge due its resilient foam and paper substrate construction. It is likely that any attempt to sterilize by autoclave or by chemical wash would result in the destruction of the resilient foam and paper substrate cartridge.

A second example of an add-on structure is taught in U.S. Pat. No. 5,285,491 titled "Dental Film Packet," by Wilfried Muylle et al., Feb. 8, 1994. Muylle et al. teaches sealing a film pack in an envelope consisting of a pair of thin pockets of injection molded plastic which are sealed with a band of adhesive tape. The envelope has no sharp edges and generally rounded corners. Thus, as with Jackson's device, this device requires manual insertion of the packet, adds significant bulk to the packet, enhances the possibility of triggering a gag reflex in the patient, and can also be reused in a non-sanitary manner.

U.S. Pat. No. 1,631,497 titled "Dental X-ray Film Package," by Harry L. Marler, Jun. 7, 1927. Marler teaches a dental x-ray film package wherein a sensitized sheet is sandwiched between two opaque sheets. A heavy band of rubber is stretched about the periphery of the package to hold the package securely together and to provide the light tight joint.

U.S. Pat. No. 1,537,925 titled "Dental X-ray Film Package," by Leonard M. Bolin, May 12, 1925, teaches a dental x-ray film package wherein a pair of film sheets and the cover sheet are inserted into the container. The container consists of a frame including a backing portion in an enlarged continuous beading about the periphery thereof. The beading must be forced away from the backing portion and stretched peripherally in order to insert the film sheets and cover sheet therein. The container thus serves to hold the package together and provide the light seal.

U.S. Pat. No. 4,791,657 titled "Intraoral Radiographic Film Packet," by Alan Kirsch et al., Dec. 13, 1988, teaches a dental radiographic film packet which includes soft corners for greater patient comfort. The packet is constructed by removing all material from the corners of a typical dental radiographic film packet with the exception of the film chip. Individual corner covers which are seamless pockets are then added to the four corners of the packet. The corner covers create an airspace at each corner around the edge of the film chip.

U.S. Pat. No. 2,084,092 titled "Dental Film Holder," by Ralph Kenney, Jun. 15, 1937 teaches a dental film holder that is a stretchable vellum rubber plate with integral corner pockets into which an x-ray dental packet may be manually inserted. Kenney's dental film holder is intended to be reusable.

From the foregoing it can be seen that many attempts to add a comfort enhancing feature to dental x-ray film packets resulted in structures requiring modification of individual film packets in order to receive a comfort enhancing structure. Further, such prior art attempts, particularly those seeking to provide the comfort enhancing feature via a frame, have resulted in a significant increase in bulk thereby enhancing the possibility of inducing a gag reflex.

SUMMARY OF THE INVENTION

It is therefore the object of the present invention to provide a frame with a comfort enhancing perimeter for an intraoral radiographic film packet.

It is a further object of the present invention to provide a frame with a comfort enhancing perimeter for an intraoral radiographic film packet which is sterilizable and reusable at the option of the user.

Yet another object of the present invention is to provide a frame with a comfort enhancing perimeter for an intraoral radiographic film packet which does not significantly increase the bulk of the film packet Still another object of the present invention is to provide a frame with a comfort enhancing perimeter for an intraoral radiographic film packet which lends itself to automated assembly with the film packet so that it may be supplied as a ready-to-use, assembled unit.

The foregoing and numerous other features, objects and advantages of the present invention will become readily apparent upon a review of the detailed description, claims and drawings set forth herein. These features, objects and advantages are accomplished by forming a molded frame with a rounded perimetric edge and which includes a slide-in pocket or a snap-in pocket adapted to receive a dental x-ray film packet. The frame is preferably formed by injection molding a low durometer thermoplastic material. A slide-in pocket or a snap-in pocket allows for single direction manipulation of either the film packet or the frame in order to assemble the two units together. Manual assembly is therefore a very simple matter and automated assembly is enabled. The frame provides a cushioning barrier to the hard interior components of the packet. In addition, the frame completely eliminates contact between the die cut edges of the film packet with the soft, sensitive tissue in the patient's mouth. These sharp, die-cut laminated edges of the relatively hard film packet are the principal source of discomfort to the patient. Thus, the patient's comfort is enhanced by the rounded edges and corners of the frame as well as the softer feeling, low durometer thermoplastic.

The molded frame of the present invention is also sterilizable such as by a detergent/chemical wash. In addition, depending on material selection, the molded frame is sterilizable by autoclave. For example, there are silicone elastomers available and known to those skilled in the art which can survive sterilization in an autoclave and from which the frame can be molded. Therefore, the frame of the present invention can be safely treated as disposable or reusable at the option of the user so long as proper sterilization techniques are practiced prior to reuse.

DETAILED DESCRIPTION OF THE INVENTION

Figure 1:
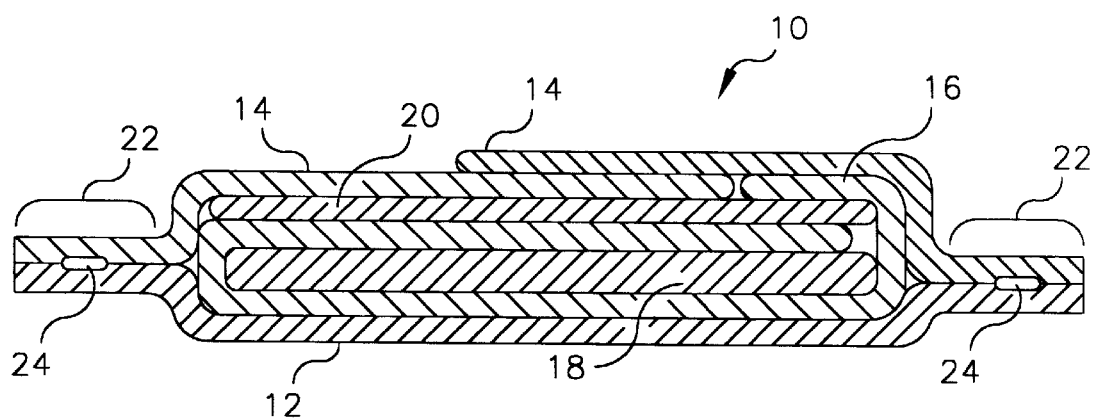
FIG. 1 is a cross-sectional view of a typical prior art dental film packet.

Turning first to FIG. 1, there is shown a cross-section of a typical prior art dental film packet 10. Dental film packet 10 includes an outer envelope comprising a vinyl sheet 12 on one face of the dental film packet 10 and a pair of overlapping vinyl sheets 14 on the opposite face thereof. Contained between the sheet 12 and overlapping sheets 14 are a paper wrap element 16, a film chip 18 and a lead foil 20. Vinyl sheets 12 and 14 project beyond dimensions of the paper wrap element 16, the film chip 18 and lead foil 20 to yield a perimetric edge 22. Laminated perimetric edge 22 allows for heat sealing of vinyl sheets 12 and 14 to one another to yield a light tight perimeter to the dental film packet 10. In addition, a heat seal 24 is generated at the overlap of vinyl sheets 14 to provide an outer envelope which is completely light tight and which is substantially watertight. This prior art dental film packet 10 therefore includes a relatively stiff and sharp perimetric edge created by the laminated perimetric edge 22. It is this relatively stiff and sharp perimetric edge which causes discomfort to the patient.

Figure 2:
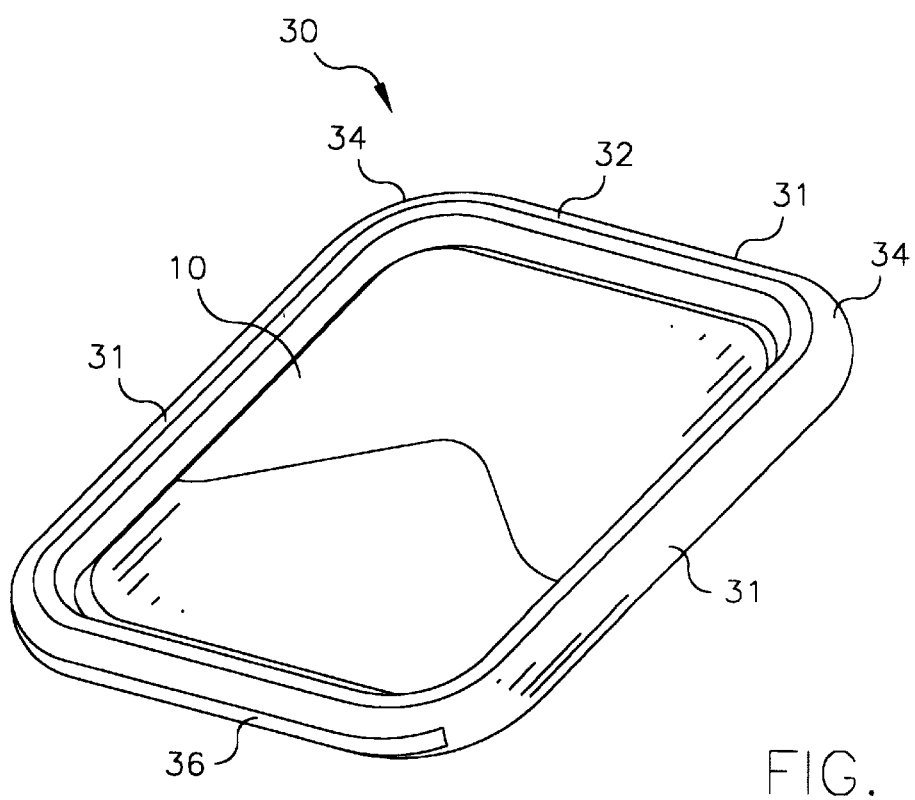
FIG. 2 is a perspective view of a first embodiment of the frame of the present invention with an intraoral radiographic film packet inserted therein.
Figure 3:
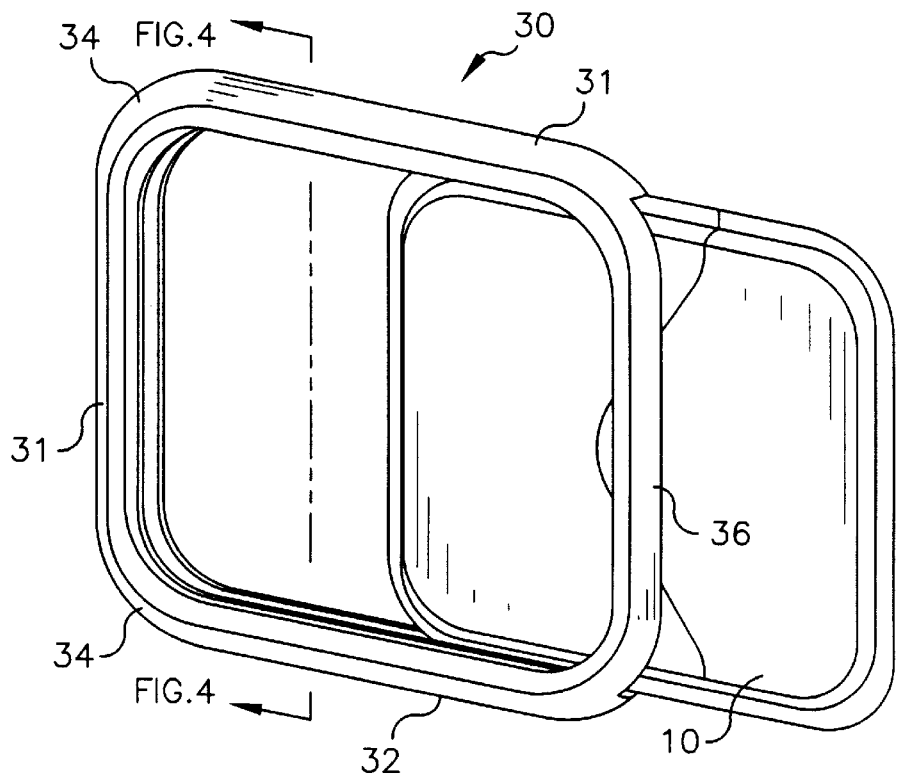
FIG. 3 is a perspective view of the frame of FIG. 2 with an intraoral radiographic film packet partially inserted therein.
Figure 4:
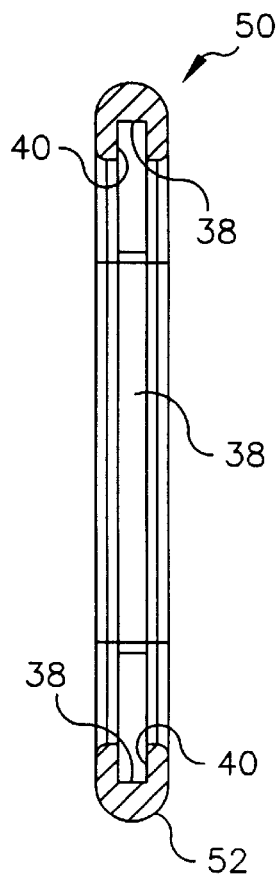
FIG. 4 is a cross-sectional view taken along lines 4—4 of FIG. 3.

Turning next FIGS. 2, 3 and 4, there is shown the first preferred embodiment of the comfort enhancing frame 30 of the present invention for holding a dental film packet 10. Frame 30 is preferably formed by injection molding with a soft thermoplastic material such as, for example, polyvinyl chloride (PVC). The thermoplastic material preferably has a relatively low durometer material (e.g. 50 to 90 Shore A) to enhance the soft feeling. Frame 30 is generally rectangular in configuration. Frame 30 includes four side members 31 with a contiguous perimetric contact surface 32 that has a generally rounded configuration in cross-section so as to provide no sharp edges that would irritate the soft/sensitive tissues inside a patient's mouth. In addition, frame 30 is rounded at each corner 34 thereof again for the purpose of eliminating sharp and/or pointed edges. There is a slotted opening 36 in one of the side members 31 adapted to receive a film packet 10. Slotted opening 36 is in alignment with interior channel 38 to thereby create a slide-in pocket. When a film packet 10 is fully inserted into frame 30, three of the four peripheral die-cut edges of the film packet 10 reside in interior channel 38. The fourth peripheral edge of the film packet 10 resides in the slotted opening 36 such that none of the sharp peripheral edges of the film packet 10 will engage the soft/sensitive tissues inside the patient's mouth. The width of the interior channel 38 is preferably such that the sides 40 (see FIG. 4) thereof will frictionally engage film packet 10 to prevent the film packet 10 from freely moving therein. In other words, film packet 10 is preferably retained in frame 30 by friction.

Figure 5:
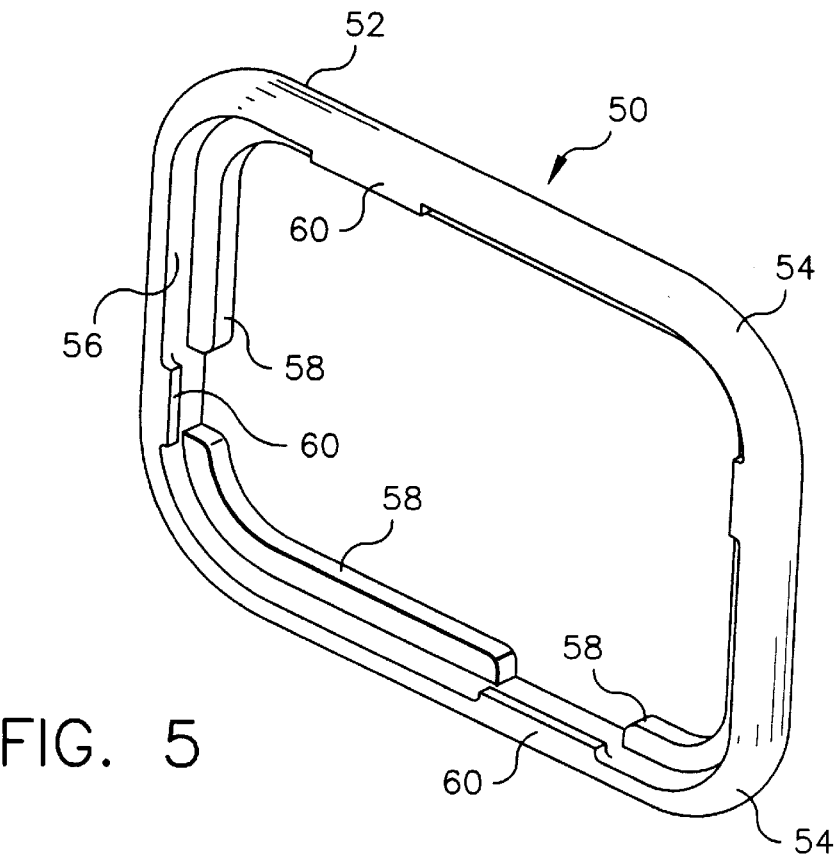
FIG. 5 is a perspective view of a second embodiment of the frame of the present invention for holding an intraoral radiographic film packet.
Figure 6:
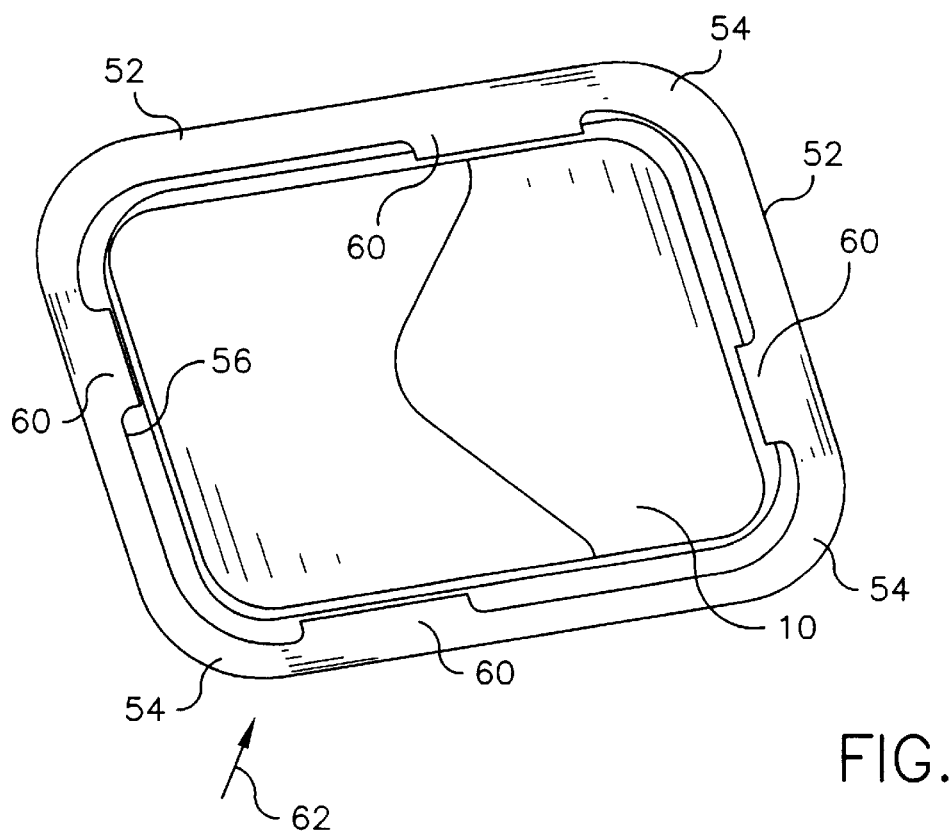
FIG. 6 is a perspective view of a second embodiment of the frame of the present invention with an intraoral radiographic film packet inserted therein.

Looking next FIGS. 5 and 6 there is shown a frame 50 which is an alternative embodiment to the frame 30 depicted in FIGS. 2 through 4. Frame 50 is preferably formed by injection molding with a soft thermoplastic material such as, for example, polyvinyl chloride (PVC). The thermoplastic material preferably has a relatively low durometer material (e.g. 50 to 90 Shore A) to enhance the soft feeling. Frame 50 is generally rectangular in configuration. Frame 50 includes a perimetric contact surface 52 that has a generally rounded configuration in cross-section so as to provide no sharp edges that would irritate the soft/sensitive tissues inside a patient's mouth. In addition, frame 50 is rounded at each corner 54 thereof again for the purpose of eliminating sharp and/or pointed edges. Projecting from one side of interior wall 56 of frame 50 are a plurality of lip elements 58. A single continuous lip element may be substituted for the plurality of lip elements 58 shown. However, for ease of molding, it is preferable that the lip element be discontinuous such that there are a plurality of lip elements 58. Projecting from the opposite side of interior wall 56 are at least two and preferably a plurality of snap-fit elements 60. Snap-fit elements 60 are generally located opposite the gaps between lip elements 58. The lip elements 58 in combination with snap fit elements 60 and interior wall 56 create a snap-in pocket for retaining a film packet 10 therein. Alternatively, lip elements 58 may be similar t snap-fit elements 60 such that packet 10 can be inserted into frame 30 from either side.

In order to insert a film packet 10 into frame 50, one need only push the packet 10 against the snap-fit elements 60 in the direction of Arrow 62 with enough force to cause the film packet 10 and/or the snap-fit elements 60 to deform thereby allowing the die-cut edges of packet 10 to pass by the snap-fit elements 60. In such manner, the film packet 10 is retained in frame 50 between lip elements 58 and snap-fit elements 60. Film packet 10 can be removed from frame 50 by applying enough force in the opposite direction of Arrow 62 to again cause the film packet 10 and/or the snap-fit elements 60 to deform thereby allowing the die-cut edges of packet 10 to pass by the snap-fit elements 60. As with frame 30, when a film packet 10 is fully inserted in frame 50, none of the sharp peripheral edges of the film packet 10 will engage the soft/sensitive tissues inside the patient's mouth. Instead, the rounded perimetric contact surface 52 and the rounded corners 54 directly contact the patient's mouth thereby providing enhanced comfort.

Although the molded frames 30 and 50 are described herein as preferably being formed by an injection molding process, it should be recognized that other molding processes can also be used. For example, frames 30 and 50 can be molded using a casting process, a pressure forming process, or a thermoforming process.

It should be appreciated that a film packet 10 can be opened to remove and process the film chip enclosed therein without having to first remove the frame 30 and 50. Because each frame 30 and 50 is open, the pull tab portion of overlapping sheets 14 is easily accessible without removal of the film packet 10 from the frame 30 and, 50. However, should the end user desire, the film packet 10 can be removed from the frame 30 and 50. The frame 30 and 50 can then be sterilized and re-used with a fresh film packet 10. It should also be appreciated that if the user does not wish to reuse the frame 30 and 50 and such frame 30 and 50 is sent to the film processor with the film packet 10 therein, the film processor has the option of sterilizing the frame 30 and 50 and re-using it with new film packets 10.

Those skilled in the art will recognize that there are two versions of dental x-ray film packets. One is composed of layers of soft thermoplastic sheets between which film, cardboard and a lead barrier are sealed. A second version uses stiff paper for the outer envelope. The stiff paper version includes the same internal elements as the thermoplastic sheet version. Both of these versions can take advantage of this invention.

Those skilled in the art will also recognize that there are now digital radiography products available which are intended to be used in place of dental x-ray film packets. One example of this type of technology uses a plate that is coated with phosphorous. When exposed to radiation, the plate will create an image that can be scanned with a laser into a computer instead of being chemically processed. To the extent that these products have the same problems of patient discomfort, the present invention can be used to solve such problems. Similarly, intraoral products which use a CCD sensor array may also achieve some level of comfort benefit through the application of the present invention.

From the foregoing, it will be seen that this invention is one well adapted to obtain all of the ends and objects hereinabove set forth together with other advantages which are apparent and which are inherent to the apparatus.

It will be understood that certain features and subcombinations are of utility and may be employed with reference to other features and subcombinations. This is contemplated by and is within the scope of the claims.

As many possible embodiments may be made of the invention without departing from the scope thereof, it is to be understood that all matter herein set forth and shown in the accompanying drawings is to be interpreted as illustrative and not in an illuminating sense.

PARTS LIST

10 dental film packet (prior art)
12 outer envelope comprising a vinyl sheet
14 outer envelope comprising overlapping vinyl sheets
16 paper wrap element
18 film chip
20 lead foil
22 laminated perimetric edge
24 heat seal
30 comfort enhancing frame (present invention)
31 side members
32 contiguous perimetric contact surface
34 rounded corners
36 slotted opening
38 interior channel
40 sides
50 comfort enhancing frame (present invention)
52 perimetric contact surface
54 rounded corners
56 interior wall
58 lip elements
60 snap fit elements

What is claimed is:

1. A frame for holding an intraoral x-ray film packet comprising:
   (a) four integrally formed side members with a single contiguous perimetric contact surface, said perimetric contact surface having a generally rounded cross-sectional configuration,
   (b) a rounded corner at an interface between each of said four integrally formed side members; and
   (c) a pocket in said four integrally formed side members adapted to have the intraoral x-ray film packet inserted and retained therein, and removed therefrom.

2. A frame for holding an intraoral x-ray film packet as recited in claim 1 further comprising:
   a slot in one of said four integrally formed side members through which the intraoral x-ray film packet can be inserted to reside in said pocket.

3. A frame for holding an intraoral x-ray film packet as recited in claim 2 wherein:
   said pocket is an interior channel in said frame in alignment with said slot.

4. A frame for holding an intraoral x-ray film packet as recited in claim 2 wherein:
   said four integrally formed side members are injection molded thermoplastic.

5. A frame for holding an intraoral x-ray film packet as recited in claim 2 wherein:
   said four integrally formed side members are formed by molding.

6. A frame for holding an intraoral x-ray film packet as recited in claim 1 further comprising:
   (a) at least one lip element projecting from a first side of an interior peripheral wall of said four integrally formed side members; and
   (b) at least two snap-fit elements projecting on opposite sides of said interior peripheral wall of said four integrally formed side members, said interior peripheral wall, said at least one lip element, and said at least two snap-fit elements forming said pocket.

7. A frame for holding an intraoral x-ray film packet as recited in claim 1 wherein:
   there are a plurality of lip elements with adjacent ones of said plurality of lip elements being separated by a gap, each of said at least two snap-fit elements residing opposite one of said gaps.

8. A frame for holding an intraoral x-ray film packet as recited in claim 6 wherein:
   said four integrally formed side members are injection molded thermoplastic.

9. A frame for holding an intraoral x-ray film packet as recited in claim 6 wherein:
   said four integrally formed side members are formed by molding.

10. A frame for holding an intraoral x-ray film packet as recited in claim 3 wherein:
    the intraoral x-ray film packet is retained in said interior channel by friction.

* * * * *